United States Patent [19]

Kline, Jr. et al.

[11] Patent Number: 5,279,566
[45] Date of Patent: Jan. 18, 1994

[54] PROTECTIVE ASSEMBLY FOR HYPODERMIC SYRINGES

[75] Inventors: Frank E. Kline, Jr., Houston; Ronald S. Kline, Arlington, both of Tex.

[73] Assignee: Ronald S. Kline, Arlington, Tex.

[21] Appl. No.: 995,838

[22] Filed: Dec. 23, 1992

[51] Int. Cl.⁵ ............................................. A61M 5/00
[52] U.S. Cl. ............................... 604/110; 604/198
[58] Field of Search ............... 604/110, 187, 192, 198, 604/263

[56] References Cited

U.S. PATENT DOCUMENTS

| | | | |
|---|---|---|---|
| 4,655,751 | 4/1987 | Harbaugh | 604/198 |
| 4,681,567 | 7/1987 | Masters et al. | 604/198 |
| 4,929,237 | 5/1990 | Medway | 604/198 |
| 4,935,016 | 6/1990 | Deleo | 604/263 X |
| 5,108,378 | 4/1992 | Firth et al. | 604/192 |

*Primary Examiner*—John D. Yasko
*Attorney, Agent, or Firm*—Charles W. McHugh

[57] ABSTRACT

A hypodermic syringe apparatus characterized by having an after-use condition which fosters safe handling—by virtue of the fact that the needle-part of the apparatus can be easily enshrouded in a protective member that is at least semi-rigid. A syringe has an elongated barrel with a generally cylindrical shape and a smooth longitudinal bore that is sized to receive a plunger; the barrel's outer surface is not circular. A protective shroud that is at least semi-rigid surrounds the barrel. The shroud has a length that is about the same as that of the barrel, and it has an internal shape that closely complements the external shape of the barrel. The shroud is designed to move with respect to the barrel only in a direction that is parallel to the barrel's longitudinal axis. The shroud has two principal positions: 1) a retracted position at which it is substantially coextensive with the barrel, and 2) a forward position at which it protrudes in front of the barrel for a distance that is sufficient to envelope a needle that is protruding from the forward end of the barrel. A resilient member is carried on the barrel and is biased to automatically engage the shroud when it has been moved to its forward position, so as to securely hold the shroud in a forward and needle-protecting position.

9 Claims, 2 Drawing Sheets

U.S. Patent Jan. 18, 1994 5,279,566
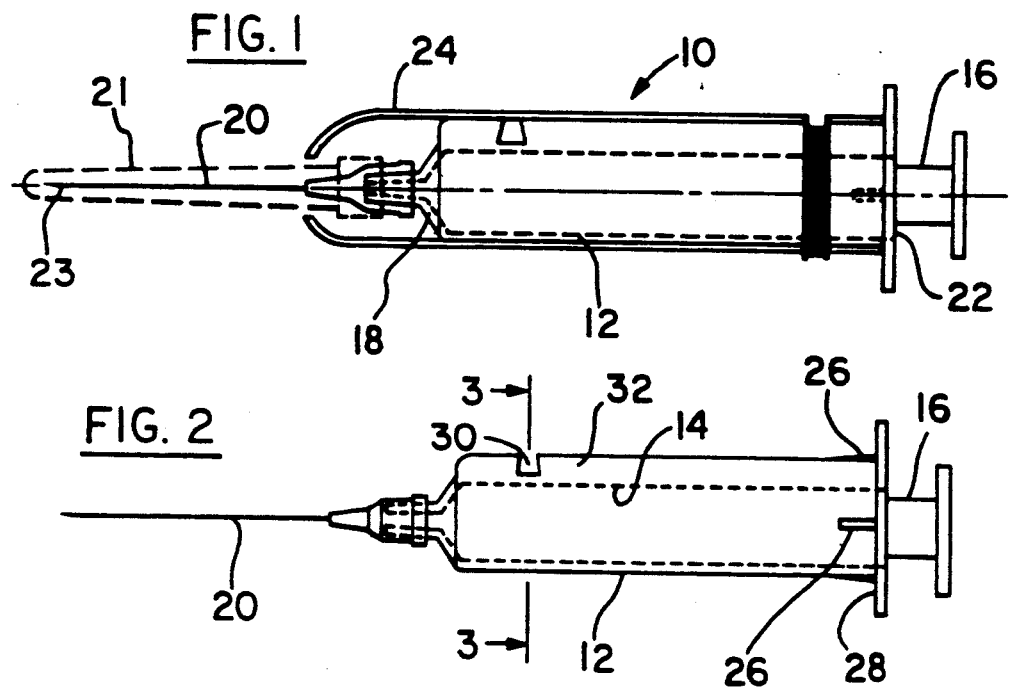
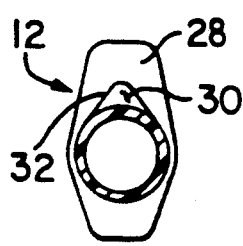
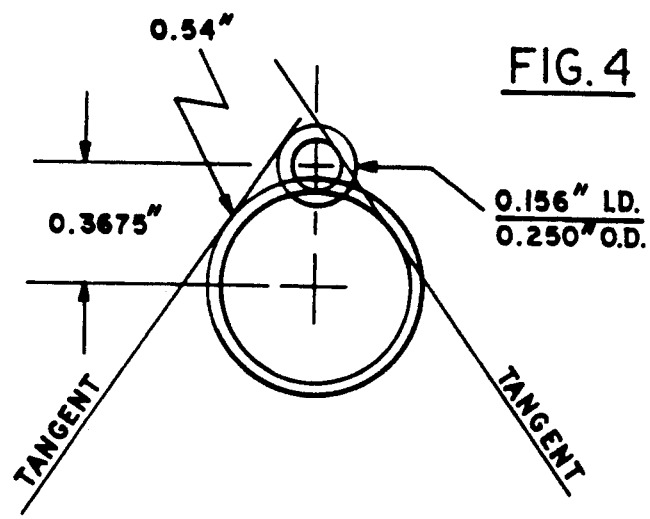
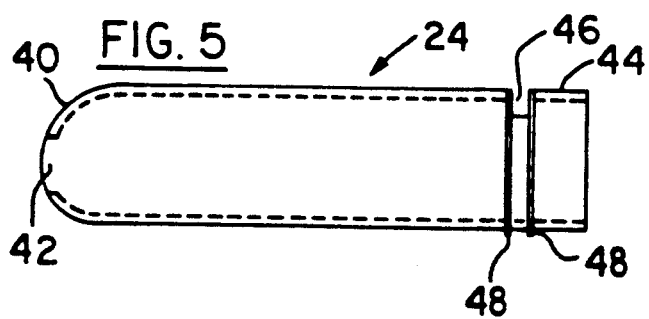
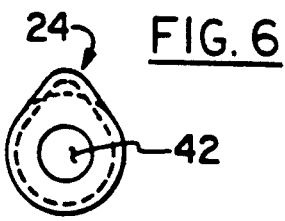

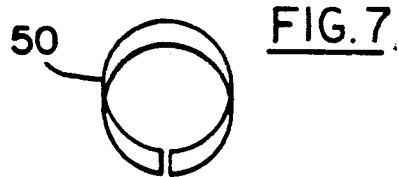
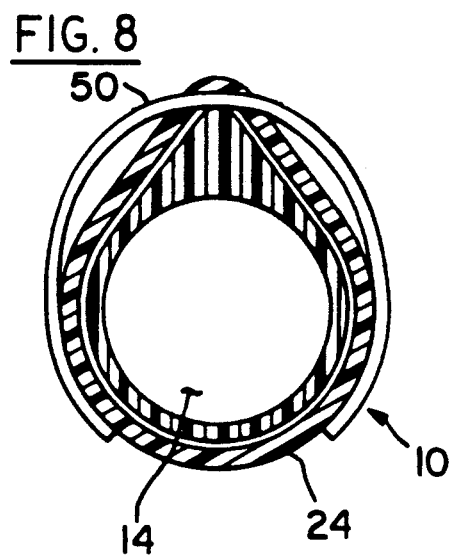
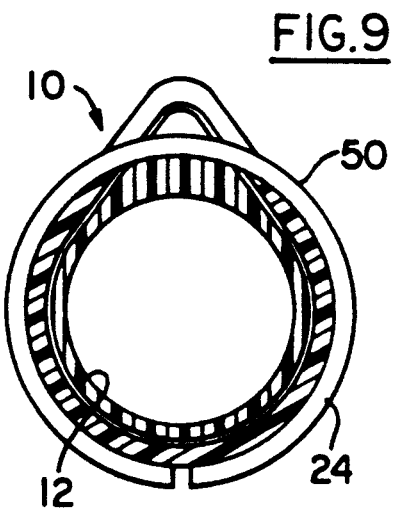
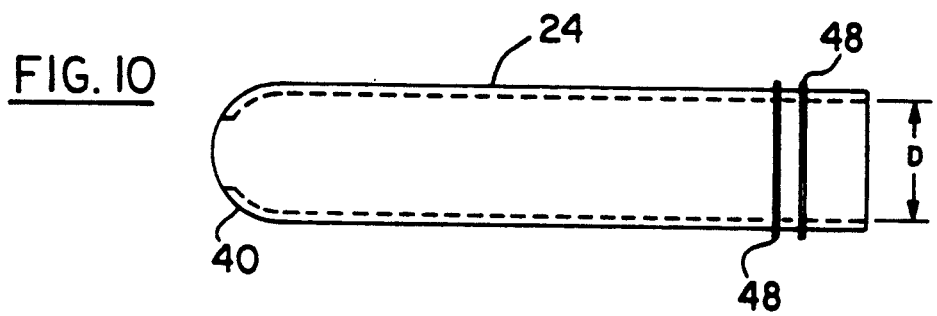
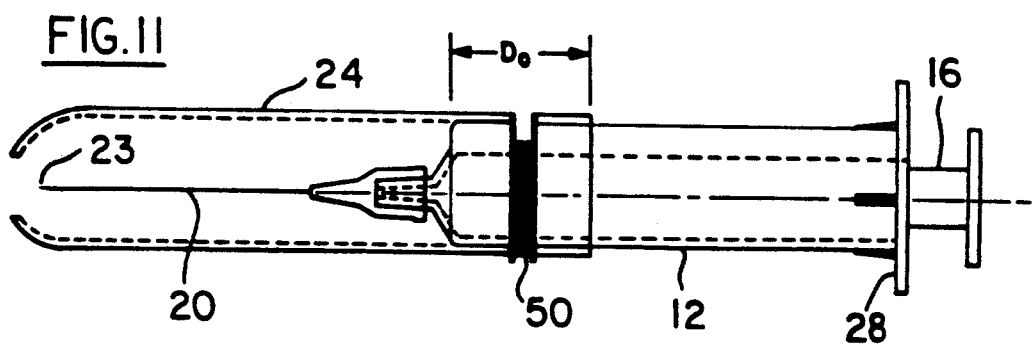

PROTECTIVE ASSEMBLY FOR HYPODERMIC SYRINGES

BACKGROUND OF THE INVENTION

This invention relates generally to hypodermic syringes of the kind that are commonly used for injecting a medication into a body or for aspirating a liquid (such as blood) from a body; more specifically, it relates to a protective device that is usable in connection with such syringes in order to protect a user from being stuck with a used needle.

Injury to users of hypodermic syringes has become of increasing concern, now that it has been well established that an accidental needle stick (involving a contaminated needle) can be enough to pass along blood-transmitted viruses such as hepatitis, herpes and acquired immunodeficiency syndrome (AIDS). Medical literature is now replete with warnings to medical personnel who handle hypodermic syringes to avoid even the slightest puncture of the skin with a used needle. Furthermore, there is an on-going risk to everyone who might come into contact with a used needle, including medical personnel and those who are involved in disposing of medical waste, etc.

The recognized risk of accidental needle sticks has prompted several persons to propose technical solutions to the problem of safe handling of used syringes and their associated needles. It is believed that the safest proposals are those which do not involve removal of the needle from the body of the syringe; to this end, it has been proposed to leave the needle in place and simply slide a tubular cover or sleeve over the needle after it has been used, so as to avoid any inadvertent contact with the needle's tip. Examples of such constructions may be found in U.S. Pat. Nos. 4,976,702 to Andrews et al. entitled "Syringe Needle Guard" and 4,998,920 to Johnson entitled "Protective Assembly For Hypodermic Syringe Devices." But while others have proposed at least some solutions, it is believed that a construction that involves the simplest and most direct action on the part of the user will be the best action. And any construction that involves a combination of required motions—such as push and twist—is not likely to be as safe as one that requires only a single motion. Hence, it is an object of this invention to provide a hypodermic syringe apparatus that has a protective sleeve that can be carried by the syringe in a stowed position where it does not interfere with normal use of the syringe—and then moved to an operative position with a single, straight-line motion.

It is another object to provide a hypodermic syringe apparatus which can be easily manufactured and assembled, but which offers the dependability of a much more sophisticated structure.

Another object is to provide an essentially fail-safe protective shield for a used needle—as long as the syringe apparatus is not subjected to the kind of deliberate abuse that could be applied with a sledge hammer or the like.

These and other objects will be apparent from a reading of the following specification and the claims appended thereto, as well as reference to the several figures of the drawing that are attached hereto.

BRIEF DESCRIPTION OF THE FIGURES OF THE DRAWING

FIG. 1 is a cross-sectioned side elevational view of a hypodermic syringe apparatus in accordance with the invention, showing the shield of the invention in a stowed position—which is the position in which the apparatus could be expected to be shipped from a factory to a user;

FIG. 2 is a side elevation view of the syringe shown in FIG. 1;

FIG. 3 is a cross-sectional view of the syringe shown in FIG. 2, taken in the plane represented by lines 3—3 in FIG. 2;

FIG. 4 is a somewhat simplified technical drawing for an exemplary embodiment of a syringe that is functional as a part of the invention;

FIG. 5 is a side elevational view of the protective shield shown in FIG. 1;

FIG. 6 is a front elevational view of the protective shield shown in FIG. 5;

FIG. 7 is a perspective view of a locking ring that is adapted to be carried by the shield, said ring being sized to engage the barrel in order to hold the shield forwardly in a needle-protecting position;

FIG. 8 is a schematic view showing the relative position of an exemplary locking ring with respect to the shield (and the barrel) when the shield is still in its retracted position;

FIG. 9 is a schematic view similar to FIG. 7 but showing the relative position of the locking ring when the shield has been moved to its most forward position;

FIG. 10 is a bottom plan view of the shield shown in FIG. 5; and

FIG. 11 is a side elevational view, partially broken away, showing the shield in its fully forward and locked position with respect to the barrel, such that the point of the needle will be precluded from errant contact with a user's skin, etc.

BRIEF DESCRIPTION OF THE INVENTION

A hypodermic syringe apparatus characterized by having an after-use condition which fosters safe handling—by virtue of the fact that the needle-part of the apparatus can be easily enshrouded in a protective member that is at least semi-rigid. As is typical of prior art devices, the apparatus includes a syringe with an elongated barrel. The barrel has a generally cylindrical shape with a smooth longitudinal bore that is sized to receive a plunger. The barrel has a forward end that is configured to engage the base of a needle, in a conventional manner. Also conventional is a plunger that can be manipulated for reciprocal movement within the barrel's bore. The forward end of the plunger has mounted thereon a circumferential member that is resilient and which is effective to create a fluid-tight seal against the barrel's bore. The plunger's second end has a conventional protrusion or knob that can be easily grasped with a person's fingers, whereby the plunger may be caused to move longitudinally with respect to the barrel.

Unlike syringes that have been so common for years, the syringe of this invention preferably has a barrel whose outer surface is not circular in cross-section. Instead, the barrel's outer surface has a longitudinal portion that is raised—which renders the surface non-circular, with the result that any adjacent member that intimately surrounds the barrel will not be able to rotate with respect to the barrel. The preferred longitudinal portion lies well outside of the wall that defines the barrel's bore, and preferably is integrally formed with the barrel. Such a longitudinal portion may be described as a longitudinal ridge that runs externally along the barrel from one end to the other, forming a rigid guide that can restrict the movement of any overlapping (i.e., telescoping) member to straight-line movement.

Mounted on and adapted to be permanently carried by the barrel is a protective shield or shroud that is made of a material that is at least semi-rigid. Like the syringe, the shroud may advantageously be made of a transparent, medical-grade polypropylene. The shroud has a length that is about the same as that of the syringe's barrel, and an over-all size that is only slightly larger than that of the barrel. The shroud has an internal shape that closely complements the external shape of the barrel, and is designed to move with respect to the barrel only in a direction that is parallel to the barrel's longitudinal axis. (Because of the non-circular shape of the barrel's exterior, the shroud cannot rotate with respect to the barrel.) The shroud has two principal positions: 1) a retracted position at which it is substantially coextensive with the barrel, and 2) a forward position at which it protrudes in front of the barrel for a distance that is sufficient to envelope a needle that is protruding from the forward end of the barrel. The shroud has a large opening at its rearward end (so that it may readily pass over the underlying barrel), and a much smaller opening at its forward end. But the shroud's forward opening must always be large enough to permit a sheath (of the kind that typically covers the tubular part of an unused needle) to pass therethrough. If and when there is a desire to change a needle, the shroud's opening should be large enough to permit the needle's hub and its associated sheath to pass through the opening.

DETAILED DESCRIPTION OF A PREFERRED EMBODIMENT OF THE INVENTION

Referring initially to FIG. 1, the invention comprises a hypodermic syringe apparatus 10 that is capable of being used in a conventional manner to inject a medication into a body, or for aspirating blood or the like from a body. By use of the term "body," it is intended to encompass humans, animals, and any other thing having the characteristics of flesh. The apparatus 10 may also be advantageously used in a laboratory or the like for handling liquids, especially when the liquids are possibly contaminated and have the potential of spreading a contagious disease if the liquids were to enter a person's bloodstream, etc. The apparatus 10 has an elongated barrel 12 with a generally cylindrical shape and a smooth longitudinal bore 14 that is sized to receive a plunger 16. The barrel 12 has a forward end 18 that is configured to engage the base or hub of a needle 20 in a conventional manner. The barrel 12 also has a second (rearward) end 22 with an opening that is large enough to freely receive the plunger 16. Prior to use, the needle 20 will typically be covered with a sheath 21 that protects the point 23 and maintains the needle in a sterile condition, etc. The sheath 21 has a throat (i.e., an entrance) whose diameter that is so very small that it is really too risky for a user to try to put the sheath back onto a used needle. So it is usually best to simply discard the sheath 21 after it has once been removed from the needle.

Mounted externally of the barrel 12 and adapted for sliding movement with respect to the barrel is a shroud or protective shield 24 made of a non-toxic and non-pyrogenic material that is generally transparent and at least semi-rigid; a suitable material for the shroud is polypropylene of the grade that is typically used to make syringes. The internal shape of the shroud 24 closely complements the external shape of the barrel 12; and the relative sizes of the barrel exterior and the shroud interior are such as to ensure a relatively tight fit (i.e., a fit that does not permit any significant kind of wobbly motion). But there must be enough clearance between the barrel and the shroud to foster a smooth relative movement between the two after the needle has been used and it is to be covered by the shroud. A diametral clearance of about 0.005 inch between the barrel exterior and the shroud interior will usually be about right.

Turning next to FIG. 2, the syringe is shown as it would appear without the protective shroud 24 mounted thereon. The barrel 12 and its associated plunger 16 and needle 20 are shown in elevation, with the needle sheath 21 has also been removed. Clearly visible in this figure are a plurality of small ramps or protuberances 26 that extend radially outward from the rear end of the barrel—for a short distance (e.g., about 0.008 inch). Four such ramps will usually be evenly distributed around the circumference of the barrel; in order to be visible, they are shown slightly exaggerated in this view. While their height is not great, it is sufficient to achieve a snug fit with the enveloping shroud 24 when the shroud is forced backward toward its most extreme rearward position—until the shroud butts against the flange 28. The orientation and size of the ramps 26 serve as a means for securely holding the shroud 24 in its retracted position until such time as it is needed. The net result is that there will be no opportunity for the shroud 24 to accidentally slide forward and interfere with use of the syringe until there is a deliberate effort on the part of the user to force the shroud forwardly. While shallow ramps 26 constitute the preferred shape for the wedging or holding devices, other shapes—such as hemispherical bumps—may also be used to advantage for holding the shroud 24 in its rearmost position.

Also clearly visible in this FIG. 2 is a recess or detent 30 in the top of the barrel—in an elongated ridge 32 that extends longitudinally for essentially the full length of the barrel. The ridge 32 is preferably integrally molded with the barrel 12, and renders the exterior surface of the barrel non-round. Hence, a shroud that is close contact with the barrel's exterior can slide longitudinally with respect to the barrel but will be prevented from rotating transversely with respect to the barrel. Referring additionally to FIG. 3 (which is a cross-sectional view taken in the plane represented by lines 3—3 in FIG. 2), it will be seen that the detent is open to the top of the ridge 32, so that it will be able to receive (at the appropriate time) a locking ring that is carried by the shroud 24. Another feature that is visible in FIG. 2 is that recess 30 is preferably trapezoidal, in that its bottom is wider (by about 50%) than its top. Therefore, when a locking ring having a thickness that is less than the depth of the recess has fallen down into the recess, the inwardly slanted walls of the recess will make it essentially impossible for the locking ring to accidentally bounce out of the recess.

In an exemplary embodiment of the syringe that is sized for accommodating five cubic centimeters (abbreviated 5 cc) of liquid, the dimensions shown in FIG. 4 are satisfactory. Thus the barrel 12 may have an outer diameter of 0.54 inch and an inner diameter of 0.48 inch. The sides of the ridge 32 can be defined by two construction lines drawn tangent to the barrel's outer surface and a small circle (e.g., 0.125 inch diameter) placed above the barrel's center. However, it should be understood that the invention described herein is not meant to be limited to any particular size or shape. Depending upon the syringe capacity that is desired (e.g., 1 cc, 3 cc, 10 cc or 20 cc, etc.), the diameter and or length of the barrel can be adjusted as necessary. However, it is recommended that one design criterion be observed in all embodiments, namely, that there be a significant overlap between the shroud and the barrel when the shroud has been moved forwardly to its needle-protecting position. It is recommended that this overlap be at least as great as the diameter of the barrel, to help ensure both longitudinal and lateral stability for the shroud 24 in its full-forward position. Even greater stability can be assured if the overlap is about one-and-a-half times the diameter of the barrel. The desired overlap can be assured in two ways: 1) by making the shroud longer than the barrel; and 2) locating the detent 30 so that there will be a desired overlap of the two parts when they become locked together. So, a designer who contemplates adjustment of the diameter or length of a barrel in order to achieve a desired syringe capacity may also want to consider an adjustment in the length of the shroud, etc.

Turning next to FIG. 5, the shroud 24 is shown from one side. The shroud 24 has a forward end 40 with an opening 42 that is at least large enough to permit the cannula of a needle to pass therethrough. Ideally, the opening 42 (shown more clearly in FIG. 6) is large enough so that the base (or hub) of a needle can be accommodated, along with any plastic sheath that is utilized in shipping and storing an unused needle. An opening diameter of about 0.325 inch will usually be adequate to meet these needs. The shroud 24 also has a transverse groove 46 near its rear end 44. The width of the groove 46 is ample to freely receive a locking ring that, in the preferred embodiment, is permanently carried by the shroud—where it is available to perform its locking function at all times. Of course, it would be possible to have a removable locking device that is handled separately and then manually installed when it is needed; such a removable device would be equivalent to, say, a cotter pin. But the risk of temporarily misplacing a locking device, so that it is not available when it is needed, seems to justify a construction in which a locking ring is permanently carried by the shroud 24. To further ensure that a locking ring will not become displaced, slightly raised ribs 48 are provided on either side of the groove 46. A suitable height for the generally circumferential ribs 48 is about 0.06 inch above the exterior surface of the shroud.

The addition of a covering shroud 24 around the barrel, or at least most of the barrel, could pose a problem for the user—unless the shroud is transparent, so that a user might still be able to see the liquid that is captured in the barrel. Therefore, the shroud 24 is preferably made of a medical grade material that is essentially polypropylene.

Turning next to FIG. 7, a preferred locking ring 50 is shown as a split ring, and it is illustrated in a relaxed condition where both of its ends are close together. Ideally, the ring 50 is made of a structural material that has a memory so that it can be distended and then automatically returned to its relaxed position when the opportunity presents itself. A preferred material for the ring 50 is tempered 302 stainless steel having a thickness of about 0.035 inch and a width of about 0.10 inch. By making the ring 50 as a split ring, and sizing it such that its "relaxed" or "memory" diameter is less than (or at least not much more than) the diameter of the barrel's inner diameter, the ring 50 will tend to snap into detent 30 just as soon as, the shroud 24 has been moved forwardly by an amount that will cause detent 30 and groove 46 to be juxtaposed. Of course, there are high strength plastics that can exhibit the same kind of resilience and springiness that is desired from a metallic ring 50. So the material of ring 50 is not critical, as long as it can resist the shear forces that may be placed on it if a syringe and an extended shroud are accidentally dropped and the assembly lands vertically on, say, someone's foot.

FIGS. 8 and 9 show the relative positions of a metal snap ring 50 and the barrel 12 and shroud 24, in both the retracted and locked positions of the shroud.

FIG. 10 shows a bottom plan view of the shroud 24, and FIG. 11 shows the same shroud as installed on a syringe and moved fully forward to its locked position with respect to the syringe. It will be seen in FIG. 11 that the cannula or tubular part of an installed needle is completely enveloped by the forwardly locked shroud; and the tip of the needle is located sufficiently far inside the shroud as to constitute no threat to a user's flesh. Furthermore, in the preferred embodiment, this "failsafe" position of the shroud is accomplished without the necessity of anything other than a single, straight-forward movement of the shroud. That is, there is no rotation or twisting of the shroud that is necessary in order to place it in a fully locked position. Such twisting or rotating that has been proposed by others is believed to be potentially hazardous in that it would be part of a two-step process, and there would always be a possibility of a user performing one step (i.e., sliding the shroud forward) but forgetting to perform the second step of rotating the shroud transversely to engage a lock. Also, the prior art "two-motion" devices inherently require strong gripping by both of a user's two hands to achieve locking. So a user that either has one hand already occupied in holding something, or has some physical infirmity that diminishes the use of one hand, will have much more trouble achieving the desired protection with devices of the prior art. Therefore, an apparatus that permits automatic locking after a sliding maneuver in a single direction is believed to be more worthy of being described as "fail-safe."

Also visible in FIG. 11 is the preferred spatial relationship between the syringe's barrel 12 and the shroud 24 when the shroud is fully forward. The overlap that exists between the barrel and the shroud is represented by the distance Do, which should be within the range of about 1.0 to 1.5 D (where D is the nominal diameter of the barrel) in order to obtain the degree of rigidity that is believed to be desirable. That is, it is believed that too many needle accidents occur when a user accidentally drops a syringe and it falls against the user's leg or foot, with the exposed needle digging into the user's flesh on its way to the floor. And even if the needle is protected by a covering shroud, the dynamic loads associated with a falling syringe could be sufficient to dislodge a protective shroud that is not strong and well anchored to a barrel's body. If a syringe assembly 10 should fall in such a way that it lands vertically (or near vertically) on someone's foot, the ring 50 could be subjected to a significant shear load; but this should not pose a problem—because of the significant shear strength that is characteristic of stainless steel and equivalent materials that are likely to be used in such an element. Of greater concern would be the possibility that the shroud or the barrel might shatter or bend about a transverse axis near the place where they overlap one another. By observing the overlap criterion of 1.0-to-1.5 D, it is believed that the assembly 10 will remain intact if it falls to the floor or bumps into some object; that is, it is believed that the shroud will achieve its desired result of shielding a used needle from errant contact with someone's flesh, etc.

Another advantage of the apparatus disclosed herein is that it helps eliminate some of the potential confusion in the minds of medical personnel when they must remember that a shroud of, say, Brand A must be pushed forward and then rotated to a locking position, while Brand B must be pushed forward and then something different must be done to achieve locking. With this apparatus, only a single straight-line motion is required.

While only the preferred embodiment has been described in great detail herein, it should be apparent to those who are skilled in the art that variations in many of the illustrated structural details could be accomplished without departing from the spirit of the invention. For example, the size and shape of the elongated ridge along the top of the barrel could be varied, or the protruding ridge could be placed on the inside of the shroud and a matching groove provided in the top of the barrel. Of course, if the relative orientations of the ridge and the groove are reversed, then the direction in which the spring "latch" moves to achieve engagement will also have to be reversed. That is, a spring will have to be oriented in such a way that it has a bias that causes it to move outwardly to engage an inwardly facing detent. Those skilled in the art will appreciate, of course, that terms like "up" and "down," "in" and "out," etc., are generally intended to be relative—not absolute—terms. Also, the preferred single and relatively large ridge on the barrel could be replaced with two or more spaced-apart and smaller ridges. The cross section of the ridge may have surface segments that are circular, parabolic, linear, etc., depending upon a particular designer's preferences in mold design and the materials that have been selected for the barrel and shroud. Because of the myriad number of possible variations that will occur to those skilled in the art, the scope of the invention should be understood to be measured only by the claims appended hereto.

What is claimed is:

1. A hypodermic syringe apparatus characterized by having an after-use condition which fosters safe handling by virtue of the fact that the needle-part of the syringe has become enshrouded in a protective member that is at least semi-rigid, comprising:
   a. an elongated barrel having a generally cylindrical shape and having a longitudinal bore that is sized to receive a plunger, said barrel having a forward end that is configured to engage the base of a needle, and said barrel having a second end which is open for receiving the plunger, and there being a longitudinal axis extending between the two ends;
   b. a plunger adapted for reciprocal movement within the barrel's bore, and said plunger having first and second ends, and there being a circumferential and resilient member near the plunger's first end and a handle near the plunger's second end;
   c. a shroud made of a material that is at least semi-rigid and having an internal shape that closely complements the external shape of the barrel, such that the shroud may be pushed in a controlled manner with respect to the barrel in a direction parallel to the barrel's longitudinal axis, and the shroud having a retracted position at which it is substantially coextensive with the barrel, and the shroud having a forward position at which it protrudes in front of the barrel for a distance that is sufficient to envelope a needle that is protruding from the forward end of the barrel, and the shroud having an opening in its forward end that is large enough to permit at least the tubular part of the needle to pass therethrough;
   d. means for preventing the shroud and the barrel from rotating transversely with respect to one another; and
   e. locking means for securely holding the shroud in a forward position with respect to the barrel after the shroud has been pushed to its forward position, and said locking means including a resilient member that is distinct from and separable with respect to the shroud and the barrel, and said resilient member having a generally ring-shaped body which is sized and configured so that it is constantly urged toward a locked position, such that the resilient member will automatically move into its locked position where the shroud has been pushed all the way to its forward position, whereby the shroud may be pushed forwardly by the user and automatically locked in a needle-enclosing position after the syringe has been used for its intended purpose.

2. The apparatus as claimed in claim 1 wherein the barrel and the shroud are made of a thermoplastic material, and the ring-shaped resilient member constitutes a metallic element that rests in a recess in the barrel when the locking means is engaged.

3. The apparatus as claimed in claim 1 wherein the shroud is made of a transparent non-pyrogenic material.

4. The apparatus as claimed in claim 1 wherein the shroud is made of a medical grade thermoplastic consisting essentially of polypropylene.

5. The apparatus as claimed in claim 1 wherein the opening in the forward end of the shroud is large enough to permit the base of a conventional needle and an attached needle sheath to pass therethrough, such that a sheathed needle may pass through the shroud opening, whereby a first sheathed needle may be removed from the apparatus and replaced with a second sheathed needle without requiring removal or displacement of the shroud.

6. The apparatus as claimed in claim 1 wherein the barrel has an outer diameter, and wherein there is a longitudinal overlap between the shroud and the barrel when the shroud has been moved to its forward position, and wherein the extent of the longitudinal overlap is within the range of about 1 to 1.5 times the outer diameter of the barrel.

7. A hypodermic syringe apparatus characterized by having an after-use condition which fosters safe handling by virtue of the fact that the needle-part of the syringe has become enshrouded in a protective member that is at least semi-rigid, comprising:
   a. an elongated barrel having a generally cylindrical shape and having a longitudinal bore that is sized to receive a plunger, said barrel having a forward end that is configured to engage the base of a needle, and said barrel having a second end which is open for receiving the plunger, and there being a longitudinal axis extending between the two ends;

b. a plunger adapted for reciprocal movement within the barrel's bore, and said plunger having first and second ends, and there being a circumferential and resilient member near the plunger's first end and a handle near the plunger's second end;

c. a shroud made of a material that is at least semi-rigid and having an internal shape that closely complements the external shape of the barrel, such that the shroud may move in a controlled manner with respect to the barrel in a direction parallel to the barrel's longitudinal axis, and the shroud having a retracted position at which it is substantially coextensive with the barrel, and the shroud having a forward position at which it protrudes in front of the barrel for a distance that is sufficient to envelope a needle that is protruding from the forward end of the barrel, and the shroud having an opening in its forward end that is large enough to permit at least the tubular part of the needle to pass therethrough;

d. means for preventing the shroud and the barrel from rotating transversely with respect to one another;

e. locking means for securely holding the shroud in a forward position with respect to the barrel after the shroud has been pushed to its forward position; and f. resilient means for constantly urging the locking means to a locked position, such that the locking means will automatically move into its locked position when the shroud has been pushed all the way to its forward position, and said resilient means including a tempered stainless steel ring, whereby the shroud may be pushed forwardly by the user and automatically locked in a needle-enclosing position after the syringe has been used for its intended purpose.

8. In connection with a hypodermic syringe construction wherein a needle is securely fastened in an operative condition at the forward end of a barrel, the method of selectively securing a protective shroud at a needle-covering position with respect to the barrel after the syringe has been used, such that the shroud may be fixed to and extend forwardly from the front end of the barrel, and such that the syringe may be safely handled without requiring a user to ever touch the needle after the needle has been used, comprising the steps of:

a. providing a shroud that is initially carried by the barrel in a retracted position where it is in intimate contact with and substantially co-extensive with the barrel while the needle extends forwardly of the barrel in an operative position, and the material of the shroud being at least semi-rigid in order that the needle may be insulated from contact with a person's skin after the shroud has been moved fully forward;

b. sliding the shroud forwardly from its retracted position after the hypodermic syringe has been used and the needle is potentially contaminated, and the extent of forward movement being sufficient to completely enshroud the needle, and the shroud material being sufficiently rigid as to render the tip of the needle incapable of making contact with a person's skin; and c. providing an automatic locking mechanism which locks the shroud against retraction just as soon as the shroud has reached a sufficiently forward position with respect to the barrel of the hypodermic syringe, and said locking mechanism including a ring-shaped resilient member that is carried externally of the shroud and is constantly biased inwardly toward a circumferential groove in the barrel's exterior, whereby the shroud may be secured in a forward and needle-covering position by virtue of being pushed in a straight-line motion from its retracted position.

9. In connection with a hypodermic syringe construction wherein a needle is securely fastened in an operative condition at the forward end of a barrel, the method of selectively securing a protective shroud at a needle-covering position with respect to the barrel after the syringe has been used, such that the shroud may be fixed to and extend forwardly from the front end of the barrel, and such that the syringe may be safely handled without requiring a user to ever touch the needle after the needle has been used, comprising the steps of:

a. providing a shroud that is initially carried by the barrel in a retracted position where it is in intimate contact with and substantially co-extensive with the barrel while the needle extends forwardly of the barrel in an operative position, and the material of the shroud being at least semi-rigid in order that the needle may be insulated from contact with a person's skin after the shroud has been moved fully forward;

b. sliding the shroud forwardly from its retracted position after the hypodermic syringe has been used and the needle is potentially contaminated, and the extent of forward movement being sufficient to completely enshroud the needle, and the shroud material being sufficiently rigid as to render the tip of the needle incapable of making contact with a person's skin; and c. providing an automatic locking mechanism which locks the shroud against retraction just as soon as the shroud has reached a sufficiently forward position with respect to the barrel of the hypodermic syringe, and the locking of the shroud against retraction being accomplished with a metallic spring member which is continuously biased against opening, whereby the shroud will be secured against accidental retraction after it has once been moved to its most forward position, and whereby the shroud may be secured in a forward and needle-covering position by virtue of being pushed in a straight-line motion from its retracted position.

* * * * *